United States Patent [19]

Dannelly

[11] 4,256,785

[45] Mar. 17, 1981

[54] PELLET COATING PROCESS

[75] Inventor: Clarence C. Dannelly, Kingsport, Tenn.

[73] Assignee: Eastman Kodak Company, Rochester, N.Y.

[21] Appl. No.: 60,548

[22] Filed: Jul. 25, 1979

[51] Int. Cl.$^3$ .............................................. B05D 7/00
[52] U.S. Cl. ........................................ 427/222; 427/3; 427/221; 427/316; 426/89; 426/293
[58] Field of Search .......................... 426/89, 293, 303; 427/212, 220, 221, 222, 316

[56] References Cited

U.S. PATENT DOCUMENTS

| | | | |
|---|---|---|---|
| 2,592,747 | 4/1952 | Schumann | 427/316 |
| 3,880,566 | 4/1975 | Komarek | 425/362 |
| 4,024,304 | 5/1977 | Smock | 427/316 |

*Primary Examiner*—Sam Silverberg
*Attorney, Agent, or Firm*—John F. Stevens; Daniel B. Reece III

[57] ABSTRACT

Coated pellets are produced by forming pellets having about 20% or more void space, contacting the pellets with a suspension of polymeric particles, reducing the temperature of the particles to create a pressure differential between the voids and the atmosphere to draw in liquid from the suspension and filter polymeric particles on the surface to form a coating.

5 Claims, No Drawings

PELLET COATING PROCESS

BACKGROUND OF THE INVENTION

1. Field of the Invention

This invention relates to the formation of polymeric coatings on the surface of pellets or other aggregates of particulate matter.

2. Description of the Prior Art

Many processes are known in the art for formation of various types of coatings on the surfaces of pellets. Such processes include dipping, rolling, brushing, air suspension, fluidized bed and spraying, to name a few. The present invention provides a method for coating pellets which contain void spaces from a suspension of thermoplastic polymeric particles in a liquid, by creating a pressure differential between the void spaces and the outside of the pellet while it is in contact with the suspension, to form a layer of polymeric particles on the surface of the pellet, and subsequently fusing or thermally adhering the particles to form a generally continuous coating.

BRIEF DESCRIPTION OF THE INVENTION

According to the present invention, coated pellets are produced by first forming pellets which contain about 20% or more by volume of void space. The surfaces of the pellets are then contacted with a polymeric material suspended in a volatile liquid. Next, the temperature of the pellets is lowered while in contact with the suspended polymeric material by an amount sufficient for the liquid from the suspension to be drawn into the void spaces as the outer surface of the pellets filters and separates polymer particles to form a surface coating. The pellets may then be heated to dry the pellets and fuse or thermally bond the polymer particles.

DETAILED DESCRIPTION OF THE INVENTION

The method according to this invention comprises the steps of first forming pellets which contain about 20% or more by volume of voids, then contacting the surface of the pellets with a polymeric material suspended in a volatile liquid and at a temperature substantially lower than the pellets. This causes a reduction in the temperature of the pellets while in contact with the suspended polymeric material by an amount sufficient for the liquid from the suspension to be drawn into the voids of the pellets as the outer surface of the pellets filters and separates polymer particles to form a surface coating therefor. It is also contemplated that the pellets may be coated with the polymeric dispersion which is at a much warmer temperature, even warmer than the pellets themselves, followed by chilling of the coated pellets to a temperature about 100° C. below the original pellet temperature.

Pellets which may be coated in accordance with the process of this invention include medicaments and nutrients adapted for oral administration to ruminant animals, as well as various other particulate aggrevates, tablets, pills, etc. Also, for purposes of this specification, vegetable seeds and other particulate matter are intended to be included within the meaning of the term "pellet". The particles to be coated may be of any suitable size and normally range from between about 0.05 in. and 0.75 in. in diameter, and may be formed by any method known in the art, such as, for example, that disclosed in U.S. Pat. No. 3,880,566.

Particles of animal feed are often made by blending the active ingredinets with microcrystalline cellulose, gum arabic, etc. Such particles may be made in accordance with U.S. Pat. No. 3,880,566, the disclosure of which is incorporated herein by reference. Measurement of void space in the particles may be made by generally accepted techniques well known in the art, such as by Archimedes principal.

The pellets may contain suitable amounts of other materials, such as coacervating salts for aiding in the formation of the coating on the surface, polymers, or liquids.

Once the pellets are prepared having a void space of at least about 20% by volume, the pellets are contacted with a dispersion of polymeric particles which is at a temperature at least about 75° C. lower than the temperature of the pellets. Preferably, the pellets are heated from below about 25° C. to a temperature of between about 125° C. and 150° C., and then submersed in the polymeric dispersion which is at about 25° C. Rather than submersion, the pellets may be contacted with the dispersion by other means, such as by spraying, rolling, etc. As the pellets cool, molecules of gas in the void spaces contract, creating a pressure differential between the void spaces and the atmosphere, allowing atmospheric pressure to force liquid into the pellets, while the surface strains and separates polymeric particles from the liquid to form a surface coating on the pellets. Once this is accomplished, the pellets may then be treated with air to remove excess solid or liquid latex material from the surfaces. Finally, the pellets are heated in an oven whereby the polymeric particles fuse, or thermally adhere, together and the solvent evaporates to form the coating.

The polymeric dispersion is formed by well known techniques such as by the polymerization process itself, wherein a polymeric latex would be formed, or a polymeric powder may be suspended in water or a volatile liquid. Normally the polymeric particles will be very small, and the dispersion will contain from about 5 to about 50% solids by weight, preferably about 10 to about 40% solids by weight, depending on the amount of coating desired. For example, a 10% solids dispersion will deposit a coating of about 2.5%, based on the combined weight of the pellet and coating, while a 40% solids dispersion will deposit a coating of about 10% by weight. This is based on a temperature differential of about 100° C. The organic liquid dispersant may be water, or any of the well known aromatic or aliphatic volatile organic liquids such as, for example, toluene, methanol, ethanol, propanol, ketones, various esters, etc.

Any thermoplastic polymer can be utilized in the present invention as long as it can be formed into tiny particles, dispersed in water or volatile organic liquid, and the particles can be fused with the application of relatively low heat, say below about 150° C. Especially preferred are polyesters, polyolefins, polyamides, etc. Polymers of particular interest are vinyl pyridine and derivatives thereof such as 2-methyl-5-vinyl pyridine. Also of particular interest are copolymers of 2-methyl-5-vinyl pyridine and styrene.

The following examples are submitted for a better understanding of the invention.

EXAMPLE 1

A 10% solid latex consisting of a copolymer having 85% 2-methyl-5-vinyl pyridine and 15% styrene is heated to 80° C. To this latex is added heated pellets containing 20% by volume of void spaces and composed of 30% microcrystalline cellulose
60% methionine
10% gum arabic wherein the pellets are formed by extrusion of an aqueous paste of the above mixture.

The pellets prior to addition to the latex are heated to 125° C. A steady stream of pellets are then brought into contact with the aqueous latex. The pellets are removed from the latex by filtration and dried in an oven heated to 100° C. (above the glass transition temperature of the copolymer). The pellets are found to be continuously coated from the surface inward to a depth of 0.5 mm. The pellets are stable to the rumen of cattle but were rendered permeable in the above sense and therefore comprised a means of modifying or supplementing the true diet of cattle.

EXAMPLE 2

Example 1 is repeated, using a suspension coating having 20% by weight solids. It is found that a coating weight of 0.0349 grams of polymeric material is deposited, or about 5% of the weight of the pellets.

EXAMPLE 3

Example 1 is repeated, using a suspension coating having 40% by weight solids. It is found that a coating weight of 0.070 grams of polymeric material is deposited, or about 10% of the weight of the pellets.

The term "voids", or void space in pellets as used herein is intended to mean crevices between solid or liquid material in the pellets, but containing air or other gas which will contract upon cooling to create a pressure differential between the voids and ambient pressure.

Unless otherwise specified, all parts, percentages, ratios, etc., are on a weight basis.

The invention has been described in detail with particular reference to preferred embodiments thereof, but it will be understood that variations and modifications can be effected within the spirit and scope of the invention.

I claim:

1. Method of making coated particles comprising
   (a) forming particles which contain about 20% or more by volume of voids,
   (b) contacting the surface of said particles with a polymeric material suspended in a volatile liquid,
   (c) reducing the temperature of said particles while in contact with said suspended polymeric material an amount sufficient for the liquid from said suspension to be drawn into the voids of the particles as the outer surface of the particles filters and separates polymer particles to form a surface coating thereof.

2. Method according to claim 1 wherein said pellets are heated to a temperature of between about 125° C. and about 150° C. prior to being contacted by said polymeric dispersion.

3. Method according to claim 2 wherein said pellets are contacted by said polymeric dispersion at below about 25° C.

4. Method according to claim 1 wherein the coated pellets are subjected to a temperature sufficiently high to fuse the polymeric material.

5. Method according to claim 1 wherein the coating weight is between about 2 and about 15% based on the weight of the coated pellet.

* * * * *